United States Patent
Borodulin et al.

[11] Patent Number: 5,081,985
[45] Date of Patent: Jan. 21, 1992

[54] VIBRATORY METHOD AND DEVICE FOR TREATING FEMALE VOIDING DYSFUNCTIONS

[75] Inventors: German Borodulin; Maxim Persidsky, both of San Francisco; Alexander Shkolnik, San Mateo, all of Calif.

[73] Assignee: Urological Instruments Research, Inc., San Francisco, Calif.

[21] Appl. No.: 478,299

[22] Filed: Feb. 9, 1990

[51] Int. Cl.$^5$ .............................................. A61H 1/00
[52] U.S. Cl. ........................................ 128/32; 128/43; 128/52; 128/66; 128/419 E; 604/107; 604/109
[58] Field of Search ................ 128/32, 51, 52, 53, 128/61, 66, 65, 44, 43, 783, 784, 788, 419 E; 604/107-109

[56] References Cited

U.S. PATENT DOCUMENTS

| | | | |
|---|---|---|---|
| 2,201,749 | 5/1940 | Vandegrift | 604/107 |
| 3,762,411 | 10/1973 | Lloyd et al. | 128/66 X |
| 3,769,977 | 11/1973 | Victory | 128/66 X |
| 3,938,530 | 2/1976 | Santomieri | 604/105 |
| 4,607,626 | 8/1986 | Borodulin et al. | 604/105 X |
| 4,705,029 | 11/1987 | Borodulin et al. | 604/105 X |
| 4,773,400 | 9/1988 | Borodulin et al. | 604/107 X |
| 4,798,600 | 1/1989 | Meadows | 128/44 X |
| 4,911,149 | 3/1990 | Borodulin et la. | 128/32 |
| 4,942,869 | 7/1990 | Borodulin et al. | 128/43 |

*Primary Examiner*—Robert A. Hafer
*Assistant Examiner*—Brian E. Hanlon
*Attorney, Agent, or Firm*—Townsend and Townsend

[57] ABSTRACT

A vibratory method for treating female voiding dysfunctions by applying to the inner walls of the urethra radial expansion forces combined with axial friction forces. This improves blood circulation, trains the urethral sphincters, and produces massaging action on the urethral walls. A device for realization of the method comprises a probe (12) formed of two rods (16) and (18) and a drive unit (14). Drive unit (14) have two output elements, which reciprocate simultaneously in mutually opposite directions. Each rod (16, 18) is connected to a respective drive unit. On their inner or mating surfaces the rods have respective cams (32, 34) and curved grooves (36, 38). During reciprocation of the rods, the cams and grooves interact and thus provide radial expansions of probe (12). Massaging action is provided by serrations (40) which are formed on the outer surface of the rods and massage the inner walls of the urethra through application of friction forces. The rods can be made from plastic and used as a sterilized disposable unit.

13 Claims, 4 Drawing Sheets

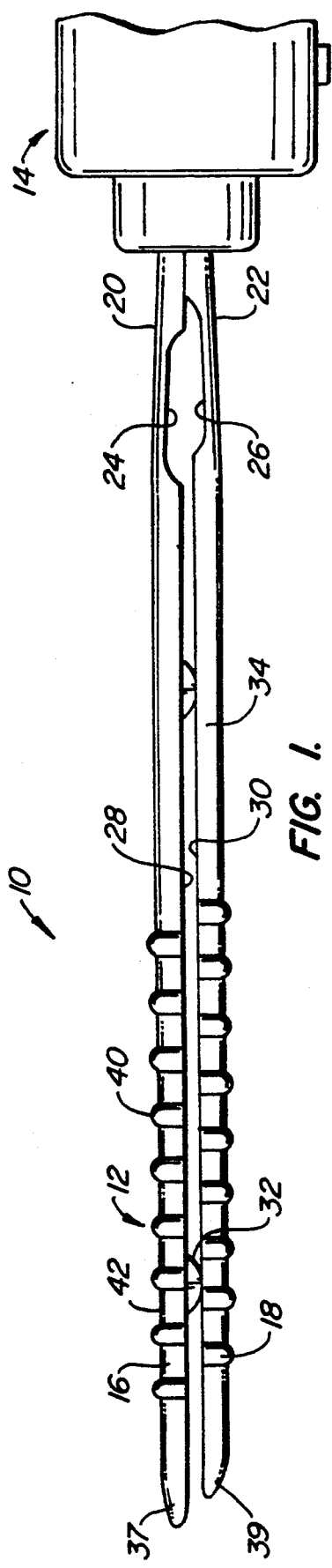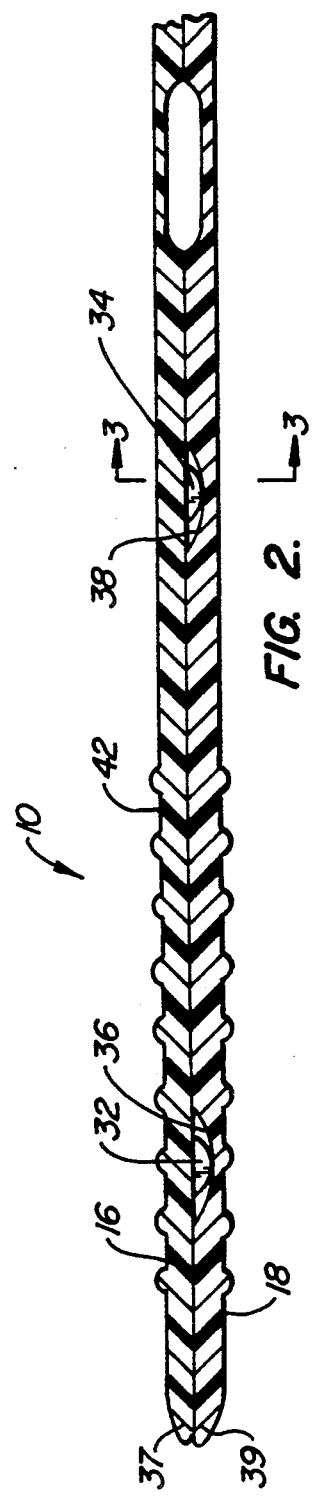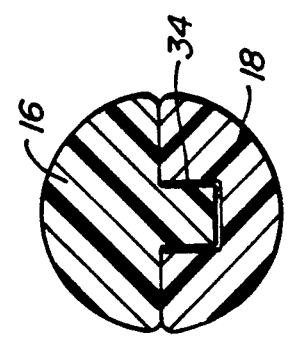

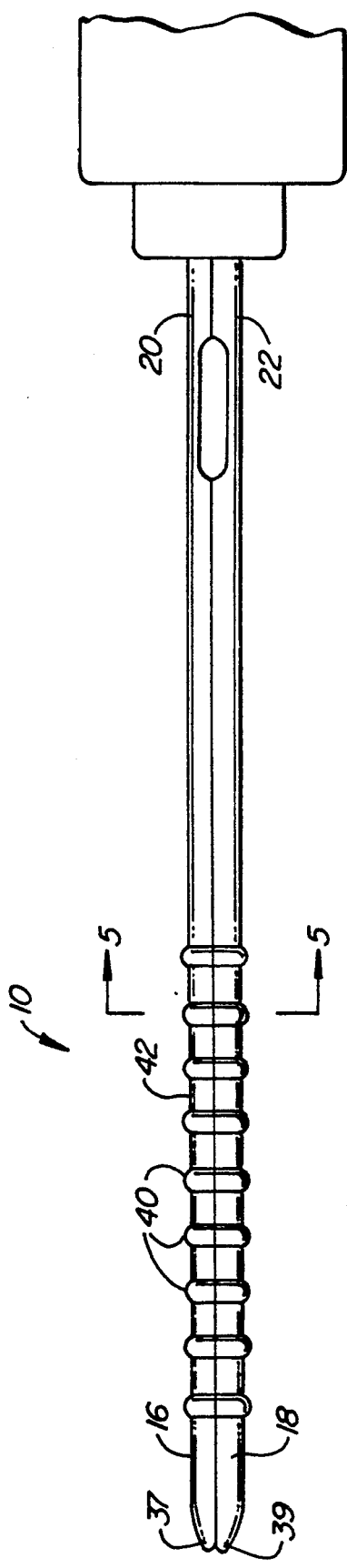
FIG. 4.
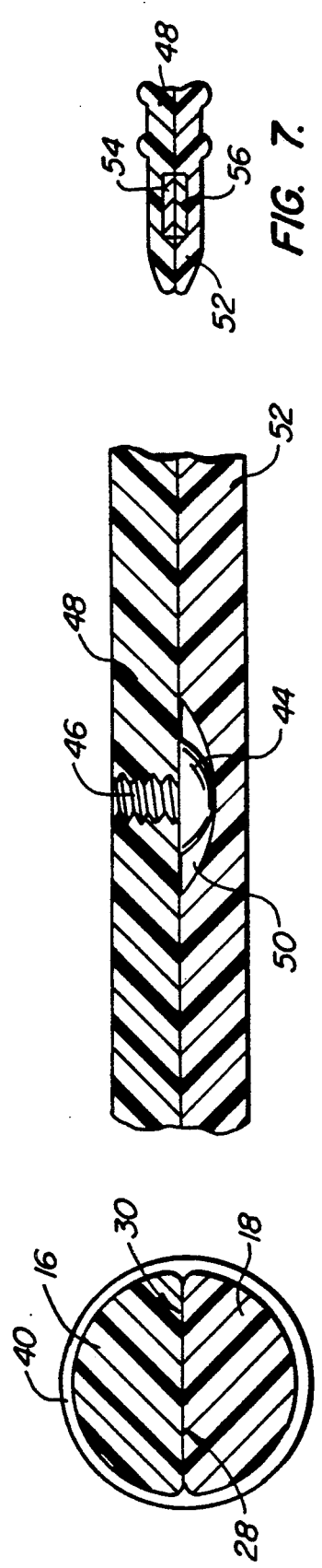
FIG. 7.
FIG. 6.
FIG. 5.

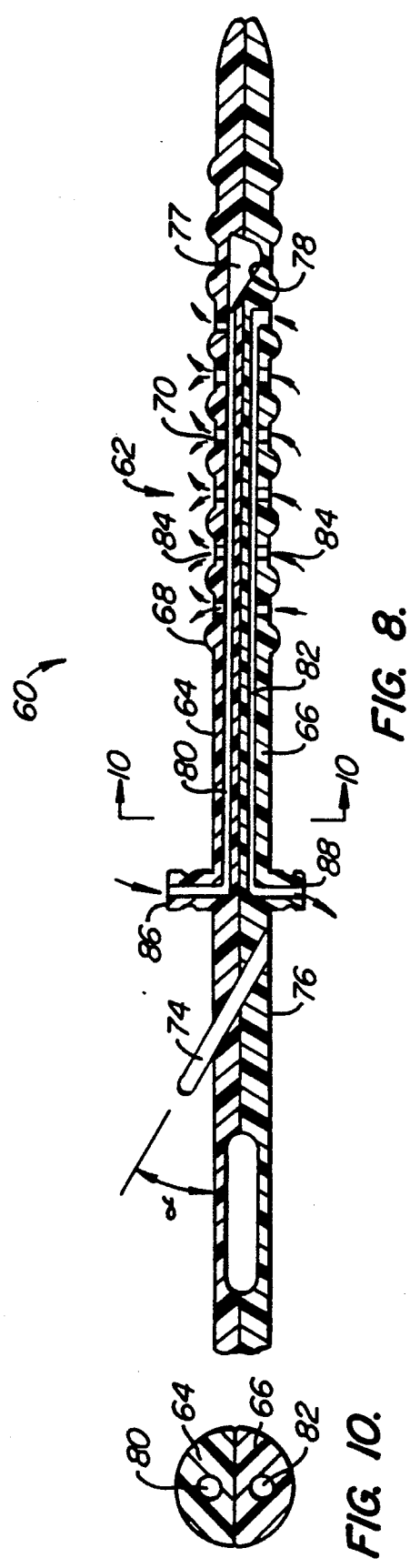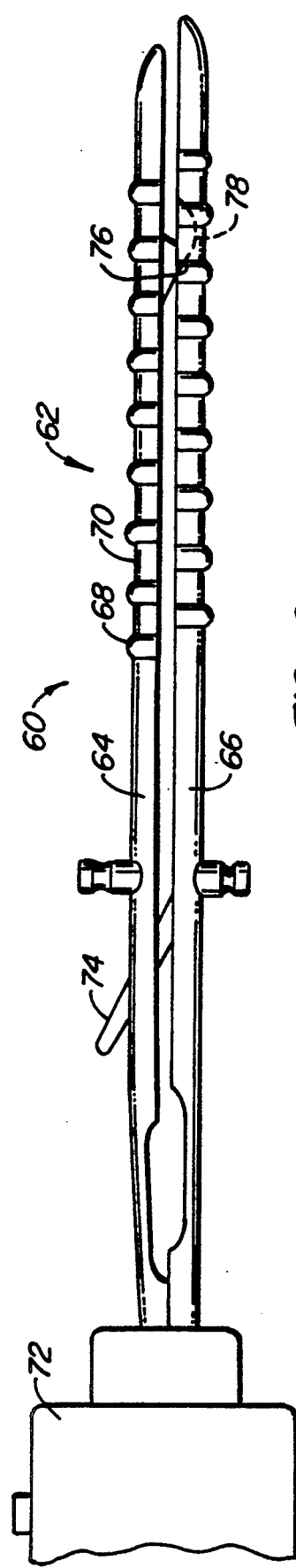
FIG. 8.
FIG. 9.
FIG. 10.

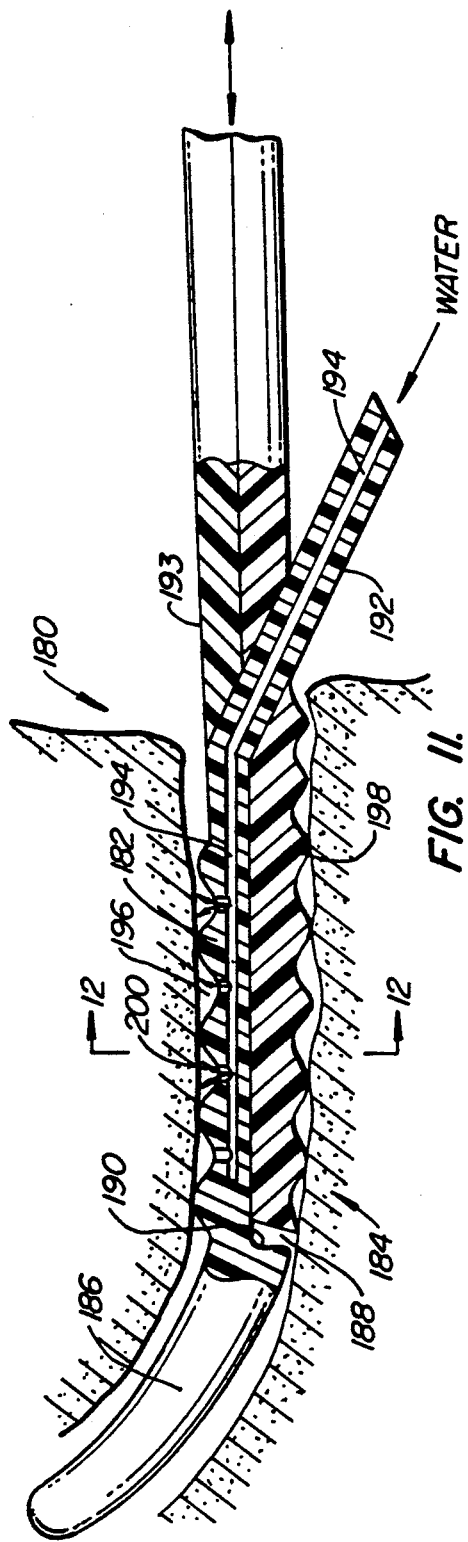
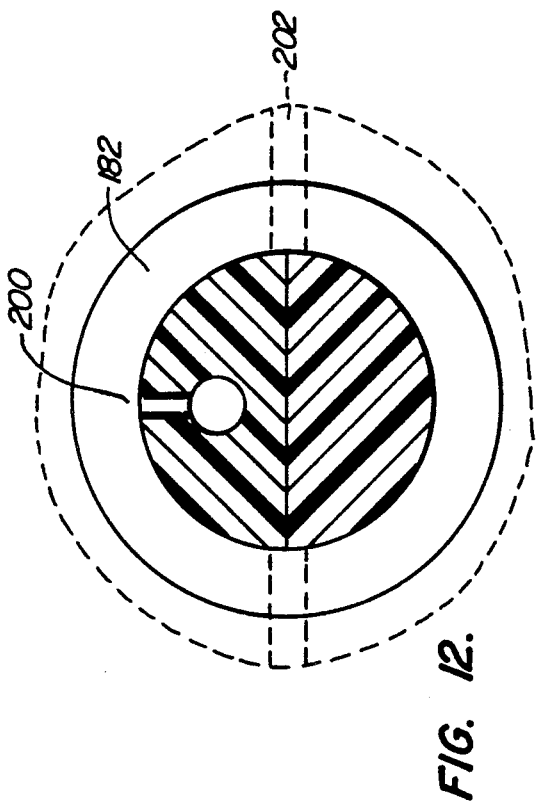
FIG. 11.
FIG. 12.

VIBRATORY METHOD AND DEVICE FOR TREATING FEMALE VOIDING DYSFUNCTIONS

BACKGROUND OF THE INVENTION

This invention is a modification of the expandable urethral bougie disclosed in U.S. Pat. No. 4,607,626, issued on Aug. 26, 1986.

The present invention relates to medical instruments, particularly to a vibratory method and device for treating female voiding dysfunctions associated with functional and organic changes in the urethra and bladder neck.

According to data from the September 1987 issue of the Journal of Urology, 20 million Americans alone suffer from some form of urinary incontinence. The economic impact of urinary incontinence is enormous and is likely to rise as the number of elderly in the population increases. In accordance with data from the Journal of Urology, April 1988, urinary incontinence in the elderly is a major social problem resulting in an annual cost of approximately $8 billion and accounts for between $0.5 to $1.5 billion in costs of nursing home care per year.

Urinary incontinence is difficult to treat. One of the most frequent types of urinary incontinence is the so-called stress urinary incontinence, which is defined as the involuntary loss of urine through the intact urethra as the result of a sudden increase in intra-abdominal pressure in the absence of bladder activity. Stress urinary incontinence accounts for roughly 75% of all female urinary incontinence. The most common cause of stress urinary incontinence in females is malfunction of the sphincteric mechanism of the urethra and an inadequate pelvic floor function.

Treatment of urinary incontinence falls into three main categories: (1) surgery; (2) drug therapy; and (3) re-education, including bladder retraining programs and re-education of the pelvic floor muscles. The existing urinary incontinence treatment methods, however, are far from being completely successful, and despite long-term and repeated courses of treatment, recurrences are not uncommon.

Accordingly, it is an object of the invention to provide a simple, reliable and efficient vibratory method for treating female voiding dysfunctions. Another object is to provide a vibratory device for treating female voiding dysfunctions. A further object is to provide a vibratory device which exerts a combined axial and radial action onto the walls of the urethra and sphincteric muscles. Still another object is to provide a vibratory device which is simple in construction, easy to manufacture, and suitable for training the sphincteric mechanism. Other advantages of the present invention will become apparent from the following description of the drawings.

BRIEF DESCRIPTION OF THE DRAWINGS

FIG. 1 is a general, side view of a device according to the preferred embodiment of the invention.

FIG. 2 is a fragmentary, longitudinal sectional view of a probe used in conjunction with the device of the invention.

FIG. 3 is a cross-sectional view taken along line III—III of FIG. 2.

FIG. 4 is a longitudinal sectional view of the probe of the device of FIG. 1 in a position where one of the rods is shifted axially with respect to another.

FIG. 5 is a cross-sectional view of the probe along line V—V of FIG. 4.

FIG. 6 is a fragmentary longitudinal sectional view of a rod with a replaceable cam.

FIG. 7 is a fragmentary sectional view of a front end of the probe incorporating holding magnets.

FIG. 8 is a longitudinal sectional view of a probe with a guide pin and flushing channels, the rods being shown in a closed position.

FIG. 9 is a side view of the probe of FIG. 8 with the rods in an open position.

FIG. 10 is a cross-sectional view along line 10—10 of FIG. 8.

FIG. 11 is a side partially broken view of a probe with a single flushing channel.

FIG. 12 is a sectional view along line 12—12 of FIG. 11.

DETAILED DESCRIPTION OF THE PREFERRED EMBODIMENT

FIG. 1 shows a vibratory device 10 of the invention, which is used for treating female voiding dysfunctions. Vibratory device 10 consists of a probe portion 12 and a drive unit or actuator 14. Actuator 14, (including its construction, method of operation, and connection to probe portion 12) is the same as described in U.S. Pat. No. 4,607,626. Preferably, actuator drive unit 14 is a commercially available device, such as a drive unit for an electric knife with two blades which reciprocate in opposite directions at adjustable speeds. The power for actuator 14 is supplied by a conventional electric power source, preferably a storage battery.

In the preferred embodiment, probe 12 is 7–8 mm in diameter and has a length of 20–25 cm. Probe 12 consists of first and second straight, flexible rods, 16 and 18. As shown in FIGS. 4 and 5, rods 16 and 18 have semi-circular cross-sections, except for the shank portions 20 and 22 which are connected to the output elements (not shown) of drive unit 14. As shown in FIGS. 2 and 3, shank portions 20 and 22 are made thinner by providing inner recesses 24 and 26 for the purpose explained below.

In a working position, i.e., when both rods 16 and 18 are inserted into drive unit 14 and connected thereto, the rods form a complete circle when seen in cross-section (FIGS. 3 and 5), except for chamfered or rounded edges at opposite sides on mating surfaces 28 and 30 of rods 16 and 18, respectively. The rounded edges prevent punching of mucosa during operation of the probe. The front end of probe 12 is also rounded.

In the preferred embodiment, rod 16 has two rounded cams 32 and 34, formed on surface 28, and rod 18 has two curved grooves 36 and 38 on surface 30. As shown in FIG. 2, the cams 32 and 34 occupy only a part of the width of the probe. In the preferred embodiment, cams 32 and 34 have a width of about ⅓ of the probe diameter. Lengthwise, cams 32 and 34 are located in the intermediate portion of the probe. In the preferred embodiment, cams 32 and 34 are spaced 6 cm to 12 cm from each other.

The depth of curved grooves 36 and 38 is between 3–4 mm and the height of cams 32 and 34 varies between 3–5 mm, depending on the depth of the grooves. Grooves 36 and 38 may have lengths from 5 mm to 12 mm depending on the desired amplitude of axial oscillations of the rods, as explained below.

The front ends 37 and 39 of rods 16 and 18, respectively, are rounded so that in an assembled state shown in FIG. 1 the ends of both rods form a smooth hemispherical surface.

On their outer surfaces, rods 16 and 18 have rounded serrations 40. In the preferred embodiment, serrations 40 are semiannuluses with rounded edges formed on rods 16 and 18. When rods 16 and 18 are in the position shown in FIGS. 2 and 4, the semiannuluses correspond to form full annuluses having circular cross-sections. Although serrations 40 may have the same width as the spaces 42 between the adjacent serrations, in the preferred embodiment spaces 42 are two to three times wider than serrations 40. The concentric configurations of the recesses and projections are shown only as an example. The serrations can also be formed by helical grooves cut on the outer periphery of the probe.

Rods 16 and 18 are formed from plastic in the preferred embodiment so that each probe can be used as a sterilized and disposable part insertable into a standard drive unit. The rods can be also made from metal, such as stainless steel.

FIG. 6 shows an embodiment with replacement cams. In that embodiment, probe 12 consists of first and second rods 48 and 52. Cam 44 is formed as a head of a screw 46 threaded into first rod 48. Cam 44 engages a curved recess 50 formed in the mating surface of second rod 52.

It is desirable to keep the front ends of rods 48 and 52 in tight contact with each other for convenience in inserting the probe. FIG. 7 shows an embodiment using magnets for holding the rods together. Permanent magnet 54 is embedded in rod 48, and permanent magnet 56 is embedded in rod 52. Preferably, magnets 54 and 56 are flexible, such as the flexible magnetic strips produced by Bunting Magnetic Co., Elk Grove Village, Ill. Alternatively, rigid magnets may be used instead. Magnets 54 and 56 hold the front ends of the rods together against movement in the radial direction, but they do not prevent them from sliding in the axial direction.

The treatment of voiding dysfunctions is conducted with the patient in the same position as in cystoscopic studies. The procedure begins with the introduction into the urethra of a special gel for lubrication and anesthesia. The bladder then filled with 150 ml of sterile saline. Probe 12 is then inserted into the urethra in the same manner as a standard metal catheter. After checking the position of the probe, drive unit 14 is switched on to begin the vibratory treatment.

Actuator 14 moves rods 16 and 18 from the center of their range of movement (as shown in FIGS. 2 and 4) axially simultaneously in opposite directions for distances corresponding to the length of grooves 36 and 38. When rod 16 moves in a forward direction and rod 18 moves in a backward direction, cams 32 and 34 slide over respective curved grooves 36 and 38 so that rods 16 and 18 move radially outwardly from each other up to a distance corresponding to the height of cams 32 and 34 or cam 44, thereby applying a radial force to the inner walls of the urethra and urethral sphincters to alternately expand and contract the urethra walls. The mucosa of the urethra walls fills spaces 42 between serrations 40 on the outer surface of each rod, so that when rods 16 and 18 move axially, the serrations rub and apply axial friction forces to the walls of the urethra, thereby producing a very effective massaging action.

After rods 16 and 18 reach the limits of their respective forward and backward movement, the actuator reverses the directions of the rods' movement, thereby moving rod 16 backward towards the actuator and moving rod 18 forward away from the actuator. The directions of the axially directed forces exerted by the rods and their serrations on the urethral walls changes. As the rods move to the center of their range of movement, the radially directed force decreases. As the rods continue their movement and go past the center of their range to the limit of their movement, the rods once again begin to move apart, thereby applying a radially outwardly directed force on the urethral walls. After reaching the limit, the directions of movements of the rods changes, thereby changing the directions of the axially directed force of the rods to the original directions and decreasing the radially outwardly directed force. The cycle is completed when the rods reach the center of their range of movement, as shown in FIGS. 2 and 4.

The frequency of this cycle may be varied to suit the application. Preferably, the frequency of the rods' movement cycle is in the range of 5 to 200 Hz.

Inner recesses 24 and 26 impart higher flexibility to the rear ends of rods 16 and 18, respectively. An increased flexibility in these portions is necessary to compensate for the deformations of the rods since the rear ends of the rods are rigidly attached to the output elements (not shown) of actuator 14 and therefore have limited freedom of movement in a radial direction.

The combined radial expansion and contraction and axial massaging action will intensify blood circulation in the urethra due to the increase in the dilation of capillaries. The increased blood flow, in turn, will create favorable conditions for higher consumption of oxygen and nutrients by muscles. It also will improve the regeneration process. The result is an improved muscular tone, elasticity and contractile capacity.

In treating dysfunctions of the sphincteric mechanism, expansions of probe 12 will cause respective expansions and constrictions of the sphincter. This, in turn, may lead to normalization of the sphincteric muscle contractility caused by the direct or reflexogenic effect of vibratory stimulation. Thus, the method and device of the invention is very effective in treating such diseases as stress urinary incontinence, urethral syndrome, and unstable bladder.

FIGS. 8–10 show a vibratory device 60 for treating voiding dysfunctions which is similar to device 10 of FIGS. 1–5 in that it consists of a probe portion 62, formed by rods 64 and 66 with serrations 68 and annular grooves 70, and an actuator 72. This embodiment, however, differs from that of FIGS. 1–5 in that it has a guide pin 74 (or pins) instead of cams 32 and 34 and incorporates a means for flushing the internal walls of the urethra during the treatment procedure.

More specifically, guide pin 74, which is arranged at an angle α to the longitudinal direction of probe 62, is fixed to one of the rods, rod 66 in the embodiment of FIGS. 8–10. In the illustrated case, pin 74 has a cylindrical configuration and is fixed to rod 66 by press-fitting into its inclined hole 76. Pin 74, however, may have any other suitable cross-section and can be attached to rod 66 by other means, e.g., by screwing into a threaded hole. Angle α may vary between 5° and 30°. The angle is selected depending on the specific purpose of the device, since this angle determines the amplitude of radial expansions of the probe in conversion of axial displacements of rods 64 and 66 into radial movements.

Since pin 74 is located in the rear portion of the probe which is not inserted into the urethra, its upper end projects beyond the outer perimeter of rod 64 far enough so that when the probe expands in the radial direction and the rods are moved apart, they are still guided by pin 74. Thus, guide pin 74 holds the rods together and prevents them from separating when they are spaced from each other in the most outwardly expanded position of the probe.

A cam 77 similar to cam 32 of the device of FIGS. 1-5 is provided in the front portion of probe 62 on one of the rods, e.g., on rod 64. Cam 77 interacts with a camming recess 78 formed in a mating rod 66.

Longitudinal channels 80 and 82 are formed in rods 64 and 66, respectively. Each channel 80 and 82 is connected to respective annular grooves 70 by holes 84. The rear end of channel 80 is connected to a pipe union 86, while the rear end of channel 82 is connected to a pipe union 88. Pipe unions 86 and 88 are made integrally with, or attached to, rod 64 at locations which are not inserted into the urethra and are in front of guide pin 74.

Pipe union 86 is connected to a source of flushing liquid supply (not shown) for flushing the interior of the urethra during treatment, while pipe union 88 is connected to a source of vacuum (also not shown).

The device of FIGS. 8-10 operates in the same manner as the device of the previous embodiment. The treatment procedure begins with the introduction into the urethra of a special gel for lubrication and anesthesia. The bladder will be filled with 150 ml of sterile saline solution. Probe 62 is then introduced into the urethra. After checking the position of the probe, drive unit 72 is switched on, and the vibratory treatment begins with combined axial and radial movements of rods 64 and 66. Rods and 66 move axially simultaneously in opposite directions. When rod 66 moves in a forward direction, i.e., away from the actuator, and rod 64 moves at the same time in the opposite direction, camming recess 78 slides over respective cam 77 at the front end of probe 62, so that rods move radially outward from each other. At the same time, inclined guide pin 74 located at the rear portion of the probe slides forward with respect to rod 64 and forces it, due to the camming action, to also move radially outwardly with respect to mating rod 66. The height of cam 77 and angle α of guide pin 74 are selected so as to provide equal relative radial movement between rods 64 and 66. During the reverse stroke, the rods move radially toward each other. When rods 64 and 66 move radially outwardly, they apply a radially outwardly directed force to the inner walls of the urethra and urethral sphincter. The serrations apply axially directed forces. The movement cycles as in the previous embodiment.

In the course of vibratory treatment procedure, flushing liquid, e.g., water, is fed either under gravity or under positive pressure, to the annular grooves 70 via pipe union 86 and longitudinal channel 80. The liquid fills the spaces defined between the inner walls of the urethra and annular grooves 70. While the rods reciprocate, the liquid is moved back and forth along the inner walls of the urethra, thus washing and cleaning the urethra. The liquid is withdrawn from the urethra via longitudinal channel 82 and pipe union 88, which is connected to the suction system (not shown). Directions of the liquid flow are shown in FIGS. 8 and 9 by arrows. In addition, some liquid may flow between the rods and out of the urethra.

FIGS. 11 and 12 show another embodiment of a device for treating voiding dysfunctions which in general is similar to the embodiment of FIGS. 8-10, and differs from it in that functions of the guide pin and the inlet pipe union are combined. More specifically, a probe 180 is formed of rods 182 and 184 which mutually reciprocate with respect to each other. One of the rods, i.e., rod 184, is shorter than the other. As shown in FIG. 11, front end 186 of rod 182 has the shape of the end of a conventional urethral bougie and is curved in the form of the urethra. In order to facilitate the insertion of probe 180, the front or pilot end 186 of rod 182 can be made from a material softer than the remaining part of the probe. It can be either replaceable or permanently connected to the rest of rod 182. If necessary, rods 182 and 184 can be made from metal, while pilot portion 186 can be made from plastic. Pilot portion 186 has essentially the same diameter as both rods together in a closed state, so that the probe preserves its wholeness as a complete cylindrical or essentially cylindrical body. There is, however, a space 188 between the front end of shorter rod 184 and the step wall 190 of pilot portion 186 of rod 182. This space 188 guarantees freedom of axial movement of rod 184 relative to rod 182 during operation of the device.

A guide pin 192 is inserted into or rigidly attached to rod 184 and, similar to the embodiment of FIGS. 8-10, is inclined at angle α to the longitudinal direction of the probe. Guide pin 192 at the same time serves as an inlet pipe union which is connected to a hose (not shown) for the supply of water or another flushing liquid. The liquid can be supplied by gravity or positively from a separate source (not shown). Pipe union/pin 192 is located at the portion of probe 193 not insertable into the urethra. A longitudinal channel 194 formed in rod 184 extends through pin 192. Channel 194 is connected to annular spaces 196 formed between serrations 198 via holes 200.

In distinction to the embodiment of FIGS. 8-10, there is only one channel in probe 180. The method for removal of the flushing liquid from the system after its use will be explained below in the description of the device operation.

The position of channel 194 is also shown in FIG. 12, which is a cross-sectional view along lines 12—12 of FIG. 11.

With regard to the vibratory action and radial and axial motions, the device of the embodiment of FIGS. 11 and 12 operates in the same manner as the one of FIGS. 8-10. Therefore this part of the operation is omitted from the description.

When a flushing liquid is supplied to annular grooves 196 from the source (not shown) of the liquid via pipe union 192, longitudinal channel 194, and holes 200, the flushing liquid fills the spaces formed between annular grooves 96 and the inner walls of the urethra. This liquid is moved back and forth while the rods reciprocate in mutually opposite directions, and when rods 182 and 184 are moved apart from each other in a radially outward direction to positions shown by broken lines in FIG. 12, a space 202 is formed between the facing surfaces of the rods. The liquid trapped in the above-mentioned spaces is discharged therefrom through space 202. This action is facilitated by reciprocations of the rods which pushes the liquid out from the urethra. If necessary, a suction means (not shown) can be provided for the removal of the waste liquid from the urethra at the point of insertion of the probe into the urethra.

The present invention has been shown and described in the form of special embodiments of the vibratory device for treating female voiding dysfunctions. It is understood, however, that these specific embodiments were given only as examples, and that many other modifications of the vibratory device of the invention are possible. For example, there can be one, three, or more cams and curved grooves. The cams may have a round or trapezoidal shape. The serrations and spaces between them may have different profiles. One rod can be stationary and another one moveable. In addition, one of the rods can be connected to one output element of the drive unit, another rod can be rigidly connected to the housing of the drive unit and serve as a guide for a core element, which is located between the rods and connected to the second output element of the drive unit. The core may have a wedge or cam for interaction with the mating surface of the first rod in order to expand the probe. The rods can be made from material other than plastic and stainless steel. With respect to the embodiments providing the flushing means, the channels introducing the fluid and/or removing the fluid may be formed on the exterior of the rods.

Although the vibratory method and device were described in conjunction with urethral sphincters, the same principle and the same device, but with the larger diameter of the probes, can be used for treating anal sphincteric dysfunctions.

What is claimed is:

1. A method for treating female voiding dysfunctions comprising:
    inserting a vibration source into a female urethra, the vibration source having means for generating cyclic radially outwardly directed forces and means for generating a cyclic axially directed force, said vibration source comprising a plurality of rods and means for actuating said rods, said means for generating an axially directed force comprising serrations formed on said rods, said serrations being in contact with the walls of said urethra;
    simultaneously applying cyclic radially outwardly directed forces and a cyclic axially directed force to said walls of said urethra, and
    introducing a flushing liquid into said urethra simultaneously with the application of said radially and axially directed forces.

2. The method of claim 1 wherein said means for generating radially outwardly directed forces comprises a cam element cooperating with said rods.

3. The method of claim 1 in which each of said rods has a first end and a second ends, wherein said first end of each rod is attached to said actuating means and said second end of each rod is free.

4. The method of claim 3 wherein the number of rods is two.

5. The method of claim 4 wherein said actuating means comprises a reciprocating element attached to said first end of each rod.

6. The method of claim 5 wherein said means for generating said radially directed force comprises a cam element cooperating with said rods.

7. The method of claim 1 wherein said flushing liquid is introduced into spaces between said serrations.

8. The method of claim 1 further comprising the step of applying suction to remove said flushing fluid from said urethra.

9. A device for treating female voiding dysfunctions by inserting it into a female urethra and simultaneously applying cyclic radially and axially directed forces comprising:
    an actuator having an output member capable of performing axial reciprocating movements;
    a probe having an outer surface, the probe comprising a plurality of rods, each of said rods having a longitudinal axis, a first end and a second end, said first end being coupled to said output member of said actuator;
    means for creating a cyclic radially outwardly directed force at the probe's outer surface in response to cyclic movement of said rods by said output member;
    means for creating a cyclic axially directed force at the probe's outer surface in response to cyclic movement of said rods by said actuator, said means for creating said axially directed force comprising serrations formed on said outer surface of said rods; and
    means for introducing flushing liquid to the probe's outer surface.

10. The device of claim 9 wherein said means for introducing flushing liquid comprises a channel formed in one of said rods, said serrations having spaces between each other and ports in said spaces communicating with said channel.

11. The device of claim 9 wherein the number of said rods is two, said means for creating said radially outwardly directed force comprises camming means on at least one of said rods.

12. The device of claim 11 wherein said camming means comprises a guide pin extending from one of said rods and a corresponding hole formed in the other rod, said guide pin being inserted into said hole, said guide pin and said hole being inclined with respect to said longitudinal direction.

13. The device of claim 9 wherein the number of said rods is two, one of the rods being shorter than the other, the second end of said longer rod having a diameter substantially equal to the combined diameter of both rods at said second end of said shorter rod, the second end of said longer rod having a higher flexibility than the remaining part of said probe and being curved in accordance with the natural shape of the urethra.

* * * * *